United States Patent [19]

Suzuki et al.

[11] Patent Number: 4,536,519
[45] Date of Patent: Aug. 20, 1985

[54] EMULSIFYING AGENT AND EMULSIFIED COSMETICS

[75] Inventors: Toshiyuki Suzuki, Sakura; Tohru Nakamura, Funabashi; Hisao Tsutsumi, Miyashiro, all of Japan

[73] Assignee: Kao Soap Co., Ltd., Tokyo, Japan

[21] Appl. No.: 386,521

[22] Filed: Jun. 9, 1982

[30] Foreign Application Priority Data

Jun. 15, 1981 [JP] Japan .................................. 56-92007
Jul. 9, 1981 [JP] Japan ................................. 56-107339

[51] Int. Cl.$^3$ ...................... A61K 31/66; A61K 47/00
[52] U.S. Cl. .................................... 514/785; 514/846; 514/847; 514/143; 514/148
[58] Field of Search .............................. 474/224, 365

[56] References Cited

FOREIGN PATENT DOCUMENTS

| | | | |
|---|---|---|---|
| 37161 | 7/1981 | European Pat. Off. | 424/224 |
| 2389671 | 12/1978 | France . | |
| 1297253 | 11/1972 | United Kingdom . | |
| 1321579 | 6/1973 | United Kingdom . | |
| 1495253 | 12/1977 | United Kingdom . | |
| 1578641 | 11/1980 | United Kingdom . | |

OTHER PUBLICATIONS

*Amer. Perfumes & Cosmetics,* Ed. 2, 119-133, (1962).

Primary Examiner—Elbert L. Roberts
Attorney, Agent, or Firm—Oblon, Fisher, Spivak, McClelland & Maier

[57] ABSTRACT

Disclosed herein is an emulsifying agent comprising (a) a partially or completely neutralized product, with a basic substance, of a phosphoric acid ester which contains a phosphoric acid monoester represented by the general formula (I) and a phosphoric acid diester represented by the general formula (II) from 100:0 to 70:30 molar ratio:

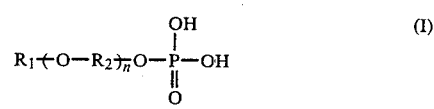

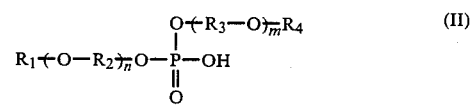

wherein $R_1$ and $R_4$ represent individually a linear alkyl group or a linear alkenyl group of 10–22 carbon atoms or a branched alkyl group of 12–24 carbon atoms, $R_2$ and $R_3$ represent individually an ethylene group or a propylene group, and m and n represent individually a number of 0–30, and (b) a nonionic surfactant with HLB of 6 or less. Emulsified cosmetics comprising (a) the neutralized product of the phosphoric acid ester, (b) a nonionic surfactant with HLB of 6 or less, (c) an oily substrate, and (d) water is also disclosed. The above emulsifying agent is weakly acidic or neutral in nature and also stable against aging degradation, it provides weakly acidic or neutral emulsified cosmetics stable at a broad pH range and confortable to skin.

10 Claims, No Drawings

EMULSIFYING AGENT AND EMULSIFIED COSMETICS

BACKGROUND OF THE INVENTION

This invention concerns a novel emulsifying agent and emulsified cosmetics using the same.

In the preparation of emulsified cosmetics, combination of higher fatty acid salts and nonionic surfactants have frequently been used as emulsifying agents therefor. However, although the emulsifying agent containing the higher fatty acid salt is excellent for attaining stable emulsification, presence of the higher fatty acid salt increases the pH value to render the cosmetic composition alkaline. By the way, the surfaces of human skins are normally covered with weakly acidic membrane (pH 4.5–6.5) and, upon contact with an alkaline substance, acidic substance is secreted to recover normal pH value of the membrane thereby maintaining its weakly acidic condition. Accordingly, it is desired that cosmetics such as creams and milky lotions applied to the skins are conditioned to weakly acidic or neutral pH.

In view of the foregoings, in the preparation of emulsified cosmetics using a higher fatty acid salt as the emulsifying agent, the addition amount of a basic substance (such as sodium hydroxide, potassium hydroxide and triethanolamine) used for neutralizing the higher fatty acid has been reduced extremely or an acidic pH buffer such as lactic acid—sodium lactate has been added after the preparation of the emulsified system, in order to reduce the pH value of the cosmetics. However, these methods are defective in that they provide poor emulsified state, which is destroyed with time to cause layer-like separation thereby significantly worsen the appearance of the cosmetics.

Further, a higher alcohol sulfate has also been used in place of the higher fatty acid salt but an emulsified system prepared therewith has a defect of giving excessively keen irritations to the skins, as well as being instable due to gradual hydrolysis of the higher alcohol sulfate with time, although the system is stable under weakly acidic or neutral conditions.

Furthermore, it has also been known that neutral or weakly acidic emulsified cosmetics can be obtained by the use of a nonionic surfactant as the emulsifying agent but, since the nonionic surfactant has only insufficient emulsifying power, it has to be used in a great amount thus causing undesirable feelings or the likes in actual use.

SUMMARY OF THE INVENTION

Under the above circumstances, the present inventor has made an earnest study fo overcoming the foregoing defects, as the result, found that an emulsifying agent consisting of a combination of a partially or completely neutralized product of particular phosphoric acid esters with a basic substance and a particular nonionic surfactant is weakly acidic or neutral in nature, comfortable to human skins and also extremely stable against aging degradation and have accomplished the present invention.

Accordingly, it is a first object of the present invention to provide an emulsifying agent comprising (a) a partially or completely neutralized product, with a basic substance, of a phosphoric acid ester which contains a phosphoric acid monoester represented by the general formula (I) and a phosphoric acid diester represented by the general formula (II) from 100:0 to 70:30 molar ratio:

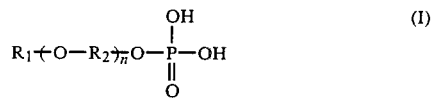

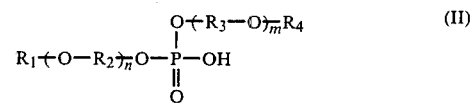

wherein $R_1$ and $R_4$ represent individually a linear alkyl group or a linear alkenyl group of 10–22 carbon atoms or a branched alkyl group of 12–24 carbon atoms, $R_2$ and $R_3$ represent individually an ethylene group or a propylene group, and m and n represent individually a number of 0–30, and (b) a nonionic surfactant with HLB or 6 or less.

Another object of this invention is to provide emulsified cosmetics comprising (a) the neutralized product of the phosphoric acid ester mentioned above, (b) a nonionic surfactant with HLB of 6 or less, (c) an oily substrate and (d) water.

DETAILED DESCRIPTION OF PREFERRED EMBODIMENTS

The phosphoric acid ester as the starting material for the neutralized product of phosphoric acid ester in this invention can further be classified into the following two groups:

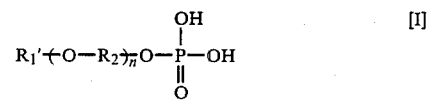

(Ia)

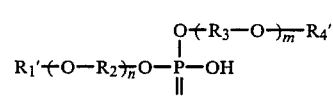

(IIa)

wherein $R_1'$ and $R_4'$ represent individually a linear alkyl group or a linear alkenyl group of 10–22 carbon atoms and $R_2$ and $R_3$ and m and n represent the same meanings as defined above.

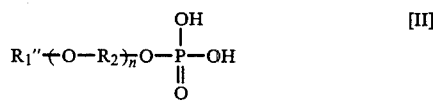

(Ib)

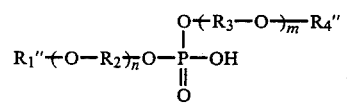

(IIb)

wherein $R_1''$ and $R_4''$ represent individually a branched alkyl group of 12–24 carbon atoms, and $R_2$ and $R_3$ and m and n represent the same meanings as defined above.

Preferred ester residues constituting the phosphoric acid ester [I] include those in which the addition mol number (m, n) of the alkylene oxide is 0, that is, linear alkyl group or linear alkenyl group, with linear alkyl group being particularly preferred. It is required that $R_1'$ and $R_4'$ have carbon atoms between 10–22. If the carbon atom number is less than 10, it gives not-favorable perfume and provides only poor emulsification. While on the other hand, if the carbon atom number is in excess of 22, crystallization occurs undesirably with time. The carbon atom number of 12–18 is particularly preferred for $R_1''$ and $R_4'$. Preferred ester residues for constituting the phosphoric acid ester [II] also include those in which the addition mol number (m, n) of the alkylene oxide is 0, that is, branched alkyl group. Further, it is required that $R_1''$ and $R_4''$ have carbon atoms between 12 and 24. If the carbon atom number is less than 12, it gives not-favorable perfume and provides only poor emulsification. While on the other hand, if the carbon atom number is in excess of 24, it provides poor emulsification, which is worsened with time. The carbon atom number of 12–18 is particularly preferred for $R_1''$ and $R_4''$. The number of branched chains and the number of carbon atoms contained therein in $R_1''$ and $R_4''$ have no particular restriction but those shown below are preferred.

(i) Methyl branched alkyl

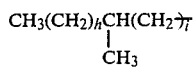

wherein h is a number of 2–14, i is a number of 3–11 and h+i is a number of 9–21, preferably 11–19.

(ii) β-branched alkyl

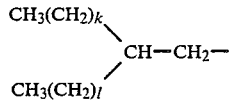

wherein k is a number of 5–11, l is a number of 3–10 and k+l is a number of 8–20, preferably 10–18.

(iii) α-branched alkyl

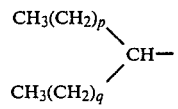

wherein p is a number of 1–20, q is a number of 1–20 and p+q is a number of 9–21, preferably 11–19.

(iv) Multi-branched alkyl group, for example,

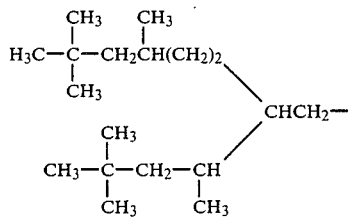

Among the above branched alkyl groups, those represented by (i) and (ii) are particularly preferred. The alcohol having the group represented by the formula (VI) is commercially available from Nissan Kagaku Kogyo K.K. as Fineoxocol 1800.

Preferred mixing ratio between the phosphoric acid monoester (I) and the phosphoric acid diester (II) is 100:0–70:30 and, particularly, 100:0–80:20 (in molar ratio). If the phosphoric acid monoester is less than 70 mol %, it worsens the emulsification, degrades the emulsified state with time to impair the appearance and significantly decrease the consistency of the cosmetics.

The basic substance used for neutralizing the phosphoric acid ester includes alkali metal hydroxide such as sodium hydroxide and potassium hydroxide; basic amino acid such as arginine, ornithine, lysine and oxylysine and alkanol amine having hydroxyalkyl group of 2 or 3 carbon atoms such as triethanolamine, diethanolamine and monoethanolamine, with the basic amino acid being particularly preferred where the phosphoric acid ester represented by the formula (Ia) or (IIa) is used.

The neutralized product of the phosphoric acid ester may be prepared by previously neutralizing a phosphoric acid ingredient with a basic substance ingredient and then blending the neutralized product upon preparation of cosmetics or by blending both of the ingredients individually upon preparation directly in the system, in situ preparation being preferred. Neutralization of the phosphoric acid ester with the basic substance may be carried out completely or partially and, further, the basic substance may be present in excess of the amount required for the neutralization. That is, the amount of the basic substance employed is selected depending on the pH of the aimed emulsification product and it is, generally, preferred to use 0.2–1.8 and, particularly, 0.4–1.0 mol of the basic substance per mol of the phosphoric acid ester.

Preferred nonionic surfactant has HLB value of 6 or less, particularly, of 2–5. The nonionic surfactant includes, for example, polyoxyalkylene alkyl (or alkenyl) ether, polyoxyalkylene alkylphenyl ether, polyoxyalkylene fatty acid ester, polyoxyalkylene glycerin fatty acid ester, polyoxyalkylene sorbitan fatty acid ester, polyoxyalkylene hardened castor oil, polyoxyalkylene alkyl amide (the oxyalkylene moiety being oxyethylene and/or oxypropylene, with oxyethylene being preferred), glycerin fatty acid ester, sorbitan fatty acid ester, sucrose fatty acid ester, polyglycerin fatty acid ester, ethylene or propylene glycol fatty acid ester, fatty acid alkanol amide (the alkyl, alkenyl and fatty acid residues preferably having 8–22, particularly, 14–18 of carbon atoms). Among them, glycerin fatty acid ester, sorbitan fatty acid ester, sucrose fatty acid ester, polyoxyethylene hardened castor oil, diglycerin fatty acid ester, ethylene or propylene glycol fatty acid ester are preferred. Particularly preferred are glycerin monostearate, glycerin mono-isostearate, sorbitan mono-stearate, sorbitan mono-oleate, sorbitan sesqui-oleate, sucrose stearate, propylene glycol mono-stearate, ethylene glycol mono-stearate, diglycerin mono-stearate, diglycerin mono-oleate, polyoxyethylene (1–3) monostearate, polyoxyethylene (2–10) hardened castor oil and the like.

Preferred emulsifying agents comprising the neutralized product of the phosphoric acid ester and the nonionic surfactant with HLB of 6 or less according to this invention include, for example, those wherein the component (a) is neutralized product of the phosphoric acid ester which contains a phosphoric acid monoester and a phosphoric acid diester represented by the following formulas in 100:0–70:30 molar ratio:

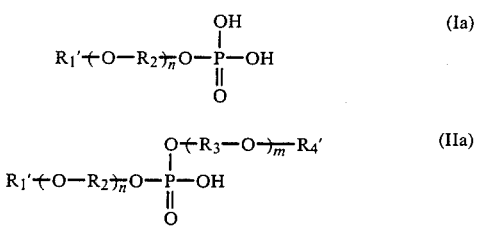

(Ia)
(IIa)

wherein $R_1'$, $R_2'$, $R_3'$, m and n have the same meanings as defined above and the component (b) is a glycerin mono-fatty acid ester.

Preferred fatty acid for constituting the glycerin mono-fatty acid ester includes those saturated or unsaturated fatty acids of linear or branched chains having carbon atoms of 8–22 and, in particular, 16–20. The glycerin mono-fatty acid ester used herein may be prepared by any process and a commercially available mixture consisting of 40–100% of glycerin mono-fatty acid ester, 0–60% of glycerin di-fatty acid ester and 0–10% of glycerin tri-fatty acid ester or the distillation product thereof can be used.

Preferred blending ratio of the glycerin mono-fatty acid ester in the emulsifying agent of the present invention is 0.1–20, particularly, 0.3–12 times by weight of the neutralized product of the phosphoric acid ester. In the case where the mixture mentioned above is used as the glycerin mono-fatty acid ester, it is blended so that the glycerin mono-fatty acid ester component contained therein lies within the above range.

The emulsifying agent according to the present invention can be used as the emulsifying agent for preparing various emulsion systems. While various processes may be employed for emulsification using this emulsifying agent, a satisfactory result can be obtained, for example, by adding to mix a neutralized product of phosphoric acid ester or phosphoric acid and a nonionic surfactant with HLB of 6 or less into an oily substance, heating to melt (for example at 70°–80° C.), agitating to homogenize and, thereafter, adding warm water or warm aqueous solution of the basic substance under agitation to thereby conduct emulsification. In this case, it is preferred to add the neutralized product of the phosphoric acid ester in an amount of 0.1–5% by weight and, particularly, 0.3–3% by weight based on the entire emulsified system. It is particularly preferred to add the phosphoric acid ester and the basic substance individually to the system and then carry out the neutralization in the system.

The emusifying agent according to the present invention, when used for the preparation of emulsified cosmetics, can provide weakly acidic or neutral emulsified cosmetics stable at a broader pH range and most confortable to skins giving no undesired irritations, which could not be obtained so far by the use of conventional higher fatty acid ester.

The emulsified cosmetics according to the present invention comprises, as essential components, (a) a neutralized product of phosphoric acid ester, (b) a nonionic surfactant with HLB of 6 or less, (c) an oily substrate and (d) water and, optionally, known cosmetic components such as other surfactant, viscosity controller, pharmaceutical agent, corrosion inhibitor, wetting agent, pigment and perfume incorporated therewith.

The oily substrate usable as the component (c) includes, for example, hydrocarbon such as liquid paraffin, paraffin wax, ceresine and squalene; wax such as bees wax, spermaceti wax, carnauba wax; natural oil and fat of animal and vegetable origin such as olive oil, tsubaki oil, jojoba oil and lanolin; silicone oil, fatty acid, higher alcohol and ester reaction products of said higher alcohol and said fatty acid.

The surfactant usable herein includes polyoxyethylene alkyl ether, polyoxyethylene fatty acid ester, polyoxyethylene sorbitan fatty acid ester polyoxyethylene sorbitol fatty acid ester, polyoxyethylene hardened castor oil alkyl sulfate, polyoxyethylene alkyl sulfate, alkyl phosphate, polyoxyethylene alkyl phosphate, fatty acid alkali metal salt, sorbitan fatty acid ester and glycerin fatty acid ester, each with HLB in excess of 6 and they may be used to such an extent as not impairing the effect of the present invention. The viscosity controller usable herein includes high molecular compound such as polyvinyl alcohol, carboxyvinyl polymer, carboxymethyl cellulose, polyvinyl pyrrolidone, hydroxyethyl cellulose and methyl cellulose; natural gum such as gelatin and tragacanth gum; and alcohol such as ethanol and isopropanol. The pharmaceutical agent usable herein includes, for example, sterilizer, antiinflammatory agent and vitamines. The wetting agent usable herein include, for example, propylene glycol, glycerin, 1,3-butylene glycol, sorbitol, lactic acid, sodium lactate and sodium pyrrolidone carboxylate. Further, corrosion inhibitor usable herein includes, for example, paraoxybenzoate, benzoic acid, sodium benzoate, sorbic acid, potassium salt of sorbic acid and phenoxyethanol.

A preferred composition for the emulsified cosmetics according to this invention is as follows:

| | Blending ratio (%) | Particularly preferred blending ratio (%) |
|---|---|---|
| Phosphoric acid ester neutralized product (a) | 0.1–5 | 0.3–3 |
| Nonionic surfactant with HLB 6 or less (b) | 0.1–20 times by weight of the component (a) | 0.3–12 times by weight of the component (a) |
| Oily substrate (c) | 1–60 | 5–35 |
| Surfactant | 0–10 | 0.5–7 |
| Viscosity controller | 0–10 | 0–2 |
| Pharmaceutical agent | 0–10 | |
| Wetting agent | 0–30 | 0–10 |
| Corrosion inhibitor or the like | 0–2 | 0.02–1 |
| Water (d) | 25–95 | 40–90 |

The emulsified cosmetics according to the present invention may be made into various forms, for example, vanishing cream, milky lotion, cold cream, cleansing cream, hair cream, foundation cream and hand cream, and they may be prepared into either oil-in-water or water-in-oil type emulsion.

The present invention will now be explained referring to the examples which, however, should not be construed as limiting the present invention thereto.

EXAMPLE 1

Emulsified systems having blending compositions as shown in Table 1 were prepared and the emulsified state and the stablility thereof were examined. The results are shown in Table 2.

TABLE 1

| Component | | This invention | Comparative products 1 | 2** |
|---|---|---|---|---|
| Oil phase | Stearyl phosphate (monoester:diester = 100:0)* | 1.2 | 1.2 | — |
| | Stearic acid | — | — | 4.0 |
| | Glycerin monostearate | 1.8 | — | — |
| | Ethyleneglycol monostearate | — | 1.8 | 2.2 |
| | Polyoxyethylene(20)sorbitan monostearate | — | — | 1.8 |
| | Liquid paraffin | 30.0 | 30.0 | 30.0 |
| Aqueous phase | Triethanolamine | — | — | 1.0 |
| | L-arginine | 0.6 | 0.6 | — |
| | Water | 66.4 | 66.4 | 61.0 |
| pH | | 6.5 | | 6.1 |

*The mixing ratio is represented by the molar ratio throughout the examples.
**After the emulsification, pH was adjusted to 6.1 by using lactic acid and sodium lactate.

Method of preparation:

The oil phase heated to 70°–80° C. and melted under agitation. The aqueous phase heated to dissolve at 70°–80° C. under agitation was added to conduct emulsification and instantly cooled to a room temperature.

Result:

TABLE 2

| | Emulsified state just after the emulsification | State left for one month at room temperature |
|---|---|---|
| This invention | good | good |
| Comparative products 1 | separated | — |
| Comparative products 2 | good | separated |

As can be seen from Table 2, the products according to this invention exhibited better emulsified state and satisfactory stability for the emulsification over a long period when compared with the comparative products which lack at least either one of the phosphoric acid ester and the glycerin mono-fatty acid ester.

EXAMPLE 2

Weakly oily moisture creams having blending compositions as shown in Table 3 were prepared and the stability for the emulsification and the viscosity were examined for aging changes. The results are shown in Table 4 and Table 5.

TABLE 3

| Component | | This invention A | This invention B | Comparative products C | Comparative products D |
|---|---|---|---|---|---|
| Oil phase | Liquid paraffin | 10.0 | 10.0 | 10.0 | 10.0 |
| | Isopropyl palmitate | 6.0 | 6.0 | 6.0 | 6.0 |
| | Cetanol | 2.0 | 2.0 | 2.0 | 2.0 |
| | Cetyl palmitate | 5.0 | 5.0 | 5.0 | 5.0 |
| | Stearyl phosphate (monoester:diester = 100:0) | 1.2 | — | — | — |
| | Cetyl phosphate (monoester:diester = 80:20) | — | 1.0 | — | — |
| | Cetyl phosphate (monoester:diester = 50:50) | — | — | 1.0 | 1.4 |
| | Glycerin monostearate | 1.8 | 2.0 | 2.0 | 1.6 |
| | Butylparaben | 0.1 | 0.1 | 0.1 | 0.1 |
| Aqueous phase | Propyleneglycol | 5.0 | 5.0 | 5.0 | 5.0 |
| | L-arginine | 0.60 | 0.38 | 0.40 | 0.34 |
| | Methylparaben | 0.1 | 0.1 | 0.1 | 0.1 |
| | Water | balance | balance | balance | balance |
| Perfume | | trace | trace | trace | trace |
| Basic substance to phosphoric acid ester molar ratio | | 1.0 | 0.8 | 1.0 | 0.6 |
| pH | | 5.8 | 5.6 | 7.4 | 6.0 |

Method of preparation:

The oil phase was heated to 70°–80° C. and melted uniformly under agitation. The aqueous phase heated to dissolve at 70°–80° C. under agitation was added to conduct emulsification. After cooled to 50° C., a perfume was added and further cooled to room temperature while stirring to obtain weakly oily moisture cream.

Result:

TABLE 4

| | | | Emulsified state just after the emulsification | Stability After 4 days | Stability After one month |
|---|---|---|---|---|---|
| This invention | A | 25° C. | good | no change | no change |
| | | 40° C. | good | no change | no change |
| | B | 25° C. | good | no change | no change |
| | | 40° C. | good | no change | no change |
| Comparative products | C | 25° C. | somewhat poor | no change | crystallized |
| | | 40° C. | somewhat poor | separated | separated |
| | D | 25° C. | good | no change | crystallized |
| | | 40° C. | good | no change | separated |

TABLE 5

| | | Viscosity (cPs, 25° C.) | |
|---|---|---|---|
| | | After 4 days | After one month |
| This invention | A | 52,000 | 56,000 |
| | B | 54,000 | 54,000 |
| Comparative products | C | 61,000 | 10,000 |
| | D | 64,000 | 32,000 |

As can be seen from Table 4 and Table 5, the weakly oily moisture creams according to the present invention showed no changes in the viscosity and satisfactory stability for the emulsification over a long period.

EXAMPLE 3

Nutritive creams having blending compositions as shown in Table 6 (O/W type) were prepared and the emulsified state and the stability thereof were examined. The results are shown in Table 7.

TABLE 6

| Component | | This invention E | This invention F | Comparative products G | Comparative products H |
|---|---|---|---|---|---|
| Oil phase | Cetyl 2-ethylhexanoate | 10.0 | 10.0 | 10.0 | 10.0 |
| | Jojoba oil | 4.0 | 4.0 | 4.0 | 4.0 |
| | Liquid lanolin | 3.0 | 3.0 | 3.0 | 3.0 |
| | Vaseline | 14.0 | 14.0 | 14.0 | 14.0 |
| | Bees wax | 5.0 | 5.0 | 5.0 | 5.0 |
| | Stearyl phosphate (monoester:diester = 90:10) | 1.4 | — | — | 1.4 |
| | Oleyl phosphate (monoester:diester = 80:20) | — | 1.8 | 1.8 | — |
| | Glycerin monopalmitate | 3.0 | 3.0 | 0.6 | 0.5 |
| | Butylparaben | 0.1 | 0.1 | 0.1 | 0.1 |
| Aqueous phase | Glycerin | 4.0 | 4.0 | 4.0 | 4.0 |
| | Propyleneglycol | 3.0 | 3.0 | 3.0 | 3.0 |

TABLE 6-continued

| | Composition (%) | | | |
|---|---|---|---|---|
| | This invention | | Comparative products | |
| Component | E | F | G | H |
| L-arginine | 0.52 | 0.71 | 0.71 | 0.52 |
| Methylparaben | 0.1 | 0.1 | 0.1 | 0.1 |
| Water | balance | balance | balance | balance |
| Perfume | trace | trace | trace | trace |
| Fatty acid monoglyceride to phosphoric acid ester weight ratio | 2.1 | 1.7 | 0.33 | 0.36 |
| pH | 5.7 | 5.8 | — | — |

Method of preparation:
The creams were prepared in the procedures similar to Example 1.
Result:

TABLE 7

| | | Emulsified state | Stability (after 3 month's leaving at room temperature) |
|---|---|---|---|
| This invention | A | good | no change |
| | B | good | no change |
| Comparative products | C | immediately separated | — |
| | D | immediately separated | — |

As can be seen from Table 7, the nutritive creams according to the present invention (O/W type) showed satisfactory emulsified state and good stability for the emulsification over a long time.

EXAMPLE 4

Nutritive milky lotions having blending compositions as shown in Table 8 (O/W type) were prepared, and the emulsified state and the stability thereof were examined. The results are shown in Table 9.

TABLE 8

| | | Composition (%) | | | |
|---|---|---|---|---|---|
| | | This invention | | Comparative products | |
| Component | | I | J | K | L |
| Oil phase | Squaline | 10.0 | 10.0 | 10.0 | 10.0 |
| | Vaseline | 2.0 | 2.0 | 2.0 | 2.0 |
| | Liquid lanolin | 2.0 | 2.0 | 2.0 | 2.0 |
| | Cetyl palmitate | 4.0 | 4.0 | 4.0 | 4.0 |
| | Cetyl phosphate (monoester:diester = 100:0) | 0.8 | 0.4 | 0.08 | 0.08 |
| | Glycerin monostearate | 1.6 | 1.2 | 1.0 | 1.6 |
| | Butylparaben | 0.1 | 1.0 | 0.1 | 0.1 |
| Aqueous phase | Propyleneglycol | 5.0 | 5.0 | 5.0 | 5.0 |
| | L-arginine | 0.40 | — | 0.05 | — |
| | L-lysine | — | 0.20 | — | 0.04 |
| | Methylparaben | 0.1 | 0.1 | 0.1 | 0.1 |
| | Water | balance | balance | balance | balance |
| | Perfume | trace | trace | trace | trace |
| pH | | 5.7 | 6.1 | 6.1 | — |

Method of preparation:
The milky lotions were prepared in the procedures similar to Example 1.
Result:

TABLE 9

| | | Emulsified state | Stability (after 3 months's leaving at room temperature) |
|---|---|---|---|
| This invention | I | good | no change |
| | J | good | no change |
| Comparative products | K | poor | separated |
| | L | immediately separated | — |

As can be seen from Table 9, the nutritive milky lotions according to the present invention (O/W type) showed satisfactory emulsified state and good stability for the emulsification over a long time.

EXAMPLE 5

Cold cream (O/W type):
Composition:

| (Oil phase) | |
|---|---|
| Vaseline | 25.0% |
| Liquid paraffin | 18.0 |
| Bees wax | 3.0 |
| Cetanol | 3.0 |
| Cetyl phosphate (monoester:diester = 100:0) | 0.6% |
| Myristyl phosphate (monoester:diester = 100:0) | 0.4 |
| Monoglycerin stearate | 2.0 |
| Butylparaben | 0.1 |
| (Aqueous phase) | |
| Propyleneglycol | 4.0 |
| L-arginine | 0.45 |
| Methylparaben | 0.1 |
| Water | balance |
| (Perfume) | trace |

Method of preparation:
The cream was prepared in the procedures similar to Example 1.

EXAMPLE 6

Nutritive cream (W/O type):
Composition:

| (Oil phase) | |
|---|---|
| Liquid paraffin | 20.0% |
| Vaseline | 12.0 |
| Bees wax | 6.0 |
| Cetyl palmitate | 5.0 |
| Liquid lanolin | 6.0 |
| Oleyl phosphate (monoester:diester = 80:20) | 0.6 |
| Monoglycerin oleate | 3.6 |
| (Aqueous phase) | |
| Propyleneglycol | 3.0% |
| Sodium benzoate | 0.5 |
| L-arginine | 0.20 |
| Water | balance |
| (Perfume) | trace |

Method of preparation:
The oil phase was heated to 70°–80° C. and uniformly melted under agitation. The aqueous phase heated to dissolve at 70°–80° C. under agitation was added to conduct emulsification. After cooled to 50° C., a perfume was added and further cooled to 30°–35° C. while stirring. Thereafter, they were further processed and sufficiently emulsified in homogenizer to obtain nutritive cream.

EXAMPLE 7

Foundation cream (O/W type):
Composition:

| (Oil phase) | |
|---|---|
| Liquid paraffin | 10.0% |
| Isopropyl myristate | 3.0 |
| Solid paraffin | 2.0 |
| Cetanol | 1.0 |
| Stearyl phosphate (monoester:diester = 100:0) | 0.8 |
| Monoglycerin stearate | 1.6 |
| Butylparaben | 0.1 |
| (Aqueous phase) | |
| Propyleneglycol | 5.0% |
| L-arginine | 0.40 |
| Montmorillonite | 1.0 |
| Titanium oxide | 7.0 |
| Talc | 5.0 |
| Iron oxide | 3.0 |
| Methylparaben | 0.1 |
| Water | balance |
| (Perfume) | trace |

Method of preparation:

The oil phase was heated to melt at 75°–80° C. and then uniformly mixed under agitation. While on the other hand, the aqueous phase was heated to dissolve at 70°–75° C. and, after uniformly dispersing the powder by a dispersing machine, they were added to the oil phase for reaction into emulsification. After cooled to 50° C. under agitation, a perfume was added, further cooled to 30°–40° C. and then processed and sufficiently emulsified on a homogenizer to obtain foundation cream.

EXAMPLE 8

For the weakly oily moisture cream A obtained Example 2, the emulsified state and the stability thereof against the aging changes were examined while varying the blending ratio of the basic substance from 0 to 2.2 (in molar ratio) to the phosphoric acid ester (stearyl monophosphate). The results are as shown in Table 10. The symbols used in the Table means: "extremely good" by ⊙, "good" by ○ and "somewhat poor" by △.

TABLE 10

| L-arginine to phosphoric acid ester molar ratio | pH | Emulsified state | Stability for emulsification Room temperature after 3 months | 40° C. after 3 months |
|---|---|---|---|---|
| 0 | — | immediately separated | — | — |
| 0.1 | — | △ | △ | separated |
| 0.4 | 5.6 | ⊙ | ⊙ | ⊙ |
| 1.0 | 6.2 | ⊙ | ⊙ | ⊙ |
| 1.8 | 6.7 | ○ | ○ | △ |
| 2.2 | — | immediately separated | — | — |

As can be seen from Table 10, moisture creams in which the molar ratio of L-arginine to the phosphoric acid ester is in the range from 0.2 to 2.0 were weakly acidic cream and satisfactory both in the emulsified state and the stability, different from those creams wherein the molar ratio is not within the range.

EXAMPLE 9

Functional test was effected by 10 expert panelers for the feeling in use with respect to the weakly oily moisture cream A in Example 2, and the nutritive cream (O/W type) E in Example 3 as the products according to the present invention, two types of comparative products P and Q having the blending compositions as shown in Table 11 and a commercially available nutritive cream R shown in Table 11, that is, five specimens in total. The results are shown in Table 12.

TABLE 11

| Component | | Composition (%) P | Q |
|---|---|---|---|
| Oil phase | Liquid paraffin | 10.0 | 10.0 |
| | Isopropyl palmitate | 6.0 | 6.0 |
| | Cetanol | 2.0 | 2.0 |
| | Cetyl palmitate | 5.0 | 5.0 |
| | Stearic acid | 2.0 | — |
| | Glycerin monostearate | 1.8 | 3.0 |
| | Butylparaben | 0.1 | 0.1 |
| Aqueous phase | Propyleneglycol | 5.0 | 5.0 |
| | Sodium dodecyl sulfate | — | 0.6 |
| | Triethanolamine | 1.0 | — |
| | Methylparaben | 0.1 | 0.1 |
| | Water | balance | balance |
| Perfume | | trace | trace |

Method of preparation:

The creams were prepared in the procedures similar to Example 2.

Result:

TABLE 12

| | | Extendability | Affinity to skin | Stickiness | Appearance |
|---|---|---|---|---|---|
| This invention | A | +1.4 | +1.8 | −1.6 | +1.4 |
| | E | +0.6 | +1.4 | −1.2 | +1.4 |
| Comparative products | P | −0.8 | −0.2 | −0.4 | +1.0 |
| | Q | +0.4 | −0.8 | +0.2 | +0.6 |
| | R (commercial product) | −1.2 | −1.0 | +1.4 | +0.2 |

(The values are averaged values for 10 personels)
(Estimation standard)

| | Extendability | Affinity to skin | Stickiness | Appearance |
|---|---|---|---|---|
| +2 | extremely good | extremely good | extremely strong | extremely good |
| +1 | fair | fair | strong | fair |
| 0 | usual | usual | usual | usual |
| −1 | poor | poor | weak | poor |
| −2 | extremely poor | extremely poor | extremely weak | extremely poor |

EXAMPLE 10

The emulsified systems having blending compositions as shown in Table 13 were prepared, and the emulsified state and the stability thereof were examined. The results are shown in Table 14.

TABLE 13

| Component | | This invention | Comparative products 1 | 2** |
|---|---|---|---|---|
| Oil phase | Isostearyl phosphate (monoester:diester = 100:0)* | 1.2 | 1.2 | — |
| | Stearic acid | — | — | 4.0 |
| | Sorbitan monostearate (HLB 4.7) | 2.0 | — | 2.2 |
| | Polyoxyethylene(20) sorbitan monostearate (HLB 14.9) | — | 2.0 | 1.2 |
| | Liquid paraffin | 30.0 | 30.0 | 30.0 |
| Aqueous phase | Triethanolamine | — | — | 1.0 |
| | L-arginine | 0.6 | 0.6 | — |
| | Water | 66.2 | 66.2 | 61.6 |

TABLE 13-continued

| | Composition (%) | | |
|---|---|---|---|
| | This | Comparative products | |
| Component | invention | 1 | 2** |
| pH | 6.5 | — | 6.1 |

*The mixing ratio is represented by the molar ratio.
**The comparative products 2 was prepared by adding lactic acid/sodium lactate after the emulsification to adjust the pH to weakly acidic range.

Method of preparation:

The oil phase was heated to 70°–80° C. and melted under agitation. The aqueous phase heated to dissolve at 70°–80° C. under agitation was added to conduct emulsification and instantly cooled to a room temperature.

TABLE 14

| | | Emulsified state just after the emulsification | State after leaving one month at room temperature |
|---|---|---|---|
| This invention | | good | good |
| Comparative products | 1 | separated | — |
| | 2 | good | separated |

EXAMPLE 11

Moisture creams having blending compositions as shown in Table 15 were prepared and the aging changes for the stabilization of the emulsification and the viscosity were examined. The results are shown in Table 16 and Table 17.

TABLE 15

| | | Composition (%) | | | |
|---|---|---|---|---|---|
| | | This Invention | | Comparative products | |
| Component | | S | T | U | V |
| Oil phase | Vaseline | 6.0 | 6.0 | 6.0 | 6.0 |
| | 2-octyldodecyl myristate | 10.0 | 10.0 | 10.0 | 10.0 |
| | Cetanol | 2.0 | 2.0 | 2.0 | 2.0 |
| | Cetyl palmitate | 6.0 | 6.0 | 6.0 | 6.0 |
| | Isostearyl phosphate* | 1.0 | — | — | — |
| | Isocetyl phosphate** | — | 1.2 | — | — |
| | Isostearyl phosphate*** | — | — | 1.0 | 1.6 |
| | Glycerin monostearate (HLB 3.5) | 2.2 | 3.0 | 2.2 | 3.0 |
| | Butylparaben | 0.1 | 0.1 | 0.1 | 0.1 |
| Aqueous phase | Glycerin | 5.0 | 5.0 | 5.0 | 5.0 |
| | Sodium hydroxide | 0.091 | 0.123 | 0.072 | 0.072 |
| | Metylparaben | 0.1 | 0.1 | 0.1 | 0.1 |
| | Water | balance | balance | balance | balance |
| Perfume | | trace | trace | trace | trace |
| Basic material to phosphoric acid ester molar ratio | | 0.8 | 0.9 | 0.8 | 0.5 |
| Emulsified state (just after emulsification) | | good | good | poor | somewhat poor |
| pH | | 5.9 | 6.2 | 7.6 | 6.2 |

*Essentially comprising those having monoester:diester ratio = 100:0 and branched chain configuration in the form of a methyl branched alkyl represented by the formula (III) with i = 9.
**Essentially comprising those having monoester:diester ratio = 80:20 and branched chain configuration in the form of a β-branched alkyl represented by the formula (IV) with k = 5 and l = 7.
***Comprising those having monoester:diester = 50:50 and branched chain configuration in the form of a methyl branched alkyl represented by the formula (III).

Method of preparation:

The oil phase was heated to 70°–80° C. and melted uniformly under agitation. The aqueous phase heated to dissolve at 70°–80° C. under agitation was added to conduct emulsification. After cooled to 50° C., a perfume was added and further cooled to room temperature while stirring to obtain moisture creams.

TABLE 16

| | | | Stability for emulsification | |
|---|---|---|---|---|
| | | | after one week | after two months |
| This invention | S | 25° C. | no change | no change |
| | | 40° C. | " | " |
| | T | 25° C. | " | " |
| | | 40° C. | " | " |
| Comparative products | U | 25° C. | partially separated | separated |
| | | 40° C. | separated | separated |
| | V | 25° C. | no change | partially separated |
| | | 40° C. | partially separated | separated |

TABLE 17

| | | Viscosity (cPs, 25° C.) | |
|---|---|---|---|
| | | after one week | after two months |
| This invention | S | 63,000 | 66,000 |
| | T | 44,000 | 42,000 |
| Comparative products | U | 47,000 | — |
| | V | 40,000 | 31,000 |

As can be seen from Table 16 and Table 17, the products according to this invention S, T wherein the phosphoric acid monoester and phosphoric acid diester are within the range of 100:0–70:30 molar ratio gave good results.

EXAMPLE 12

Nutritive creams (O/W type) having blending compositions as shown in Table 18 were prepared and the emulsified state and the stabilization for emulsification were examined. The results are shown in Table 19.

TABLE 18

| | | Composition (%) | | | |
|---|---|---|---|---|---|
| | | This invention | | Comparative products | |
| Component | | W | X | Y | Z |
| Oil phase | 2-octyldodecyl myristate | 10.0 | 10.0 | 10.0 | 10.0 |
| | Jojoba oil | 4.0 | 4.0 | 4.0 | 4.0 |
| | Liquid lanolin | 3.0 | 3.0 | 3.0 | 3.0 |
| | Vaseline | 14.0 | 14.0 | 14.0 | 14.0 |
| | Bees wax | 5.0 | 5.0 | 5.0 | 5.0 |
| | Isostearyl phosphate* | 0.8 | 1.0 | 1.0 | 1.4 |
| | Sorbitan monosteratate (HLB 4.7) | 2.4 | 2.5 | 0.08 | 0.10 |
| | Polyoxyethylene(20)sorbitan monostearate (HLB 14.9) | 0.4 | — | 2.00 | — |
| | Butylparaben | 0.1 | 0.1 | 0.1 | 0.1 |
| Aqueous phase | Glycerin | 3.0 | 3.0 | 3.0 | 3.0 |
| | Propylene glycol | 4.0 | 4.0 | 4.0 | 4.0 |
| | Potassium hydroxide | — | 0.14 | — | 0.21 |
| | L-arginine | 0.34 | — | 0.43 | — |
| | Methylparaben | 0.1 | 0.1 | 0.1 | 0.1 |
| | Water | balance | balance | balance | balance |
| Perfume | | trace | trace | trace | trace |
| Oleophilic nonionic surfactant to phosphoric acid ester weight ratio | | 3.0 | 2.5 | 0.08 | 0.07 |
| pH | | 6.0 | 6.4 | — | — |

*Comprising those having monoester:diester ratio = 90:10 and branched chain configuration in the form of a methyl branched alkyl represented by the formula (III).

Method of preparation:

The creams were prepared in the procedures similar to Example 11.

Result:

TABLE 19

| | | Emulsified state | Stability for emulsification (after 3 month's leaving at room temperature) |
|---|---|---|---|
| This invention | W | good | no change |
| | X | good | no change |
| Comparative products | Y | immediately separated | — |
| | Z | immediately separated | — |

As can be seen from Table 19, the products according to the present invention (W, X) in which the weight ratio of oleophilic nonionic surfactant to phosphoric acid ester is in the range of 0.1–20 gave good results.

EXAMPLE 13

Nutritive milky lotions (O/W type) having blending compositions as shown in Table 20 were prepared and the emulsified state and the stability for emulsification were examined. The results are shown in Table 21.

TABLE 20

| | | Composition (%) | | | |
|---|---|---|---|---|---|
| | | This invention | | Comparative products | |
| Component | | A | B | C | D |
| Oil phase | Squalene | 10.0 | 10.0 | 10.0 | 10.0 |
| | Vaseline | 2.0 | 2.0 | 2.0 | 2.0 |
| | Liquid lanolin | 2.0 | 2.0 | 2.0 | 2.0 |
| | Cetyl palmitate | 4.0 | 4.0 | 4.0 | 4.0 |
| | Isocetyl phosphate* | 0.8 | 0.4 | 0.08 | 0.08 |
| | Glycerin monostearate (HLB 3.5) | 1.6 | 1.2 | 1.0 | 1.6 |
| | Butylparaben | 0.1 | 1.0 | 0.1 | 0.1 |
| Aqueous phase | Propylene glycol | 5.0 | 5.0 | 5.0 | 5.0 |
| | L-arginine | 0.40 | — | 0.05 | — |
| | Sodium hydroxide | — | 0.04 | — | 0.01 |
| | Methylparaben | 0.1 | 0.1 | 0.1 | 0.1 |
| | Water | balance | balance | balance | balance |
| Perfume | | trace | trace | trace | trace |
| pH | | 5.9 | 6.4 | 6.1 | — |

*Essentially comprising those having monoester:diester ratio = 100:0 and branched chain configuration in the form of a β-branched alkyl represented by the formula (IV) with k = 5 and l = 7.

Method of preparation:
Milky lotions were prepared in the procedures similar to Example 11.
Result:

TABLE 21

| | | Emulsified state | Stability for emulsification (after 3 month's leaving at room temperature) |
|---|---|---|---|
| This invention | A | good | no change |
| | B | good | no change |
| Comparative products | C | poor | separated |
| | D | immediately separated | — |

As can be seen from Table 21, the products according to the present invention in which phosphoric acid ester is contained within a range of 0.1–5% gave good results.

EXAMPLE 14

The nutritive creams (W/O type) having blending compositions as shown in Table 22 were prepared and the emulsified state and the stability for emulsification were examined. The results are shown in Table 23.

TABLE 22

| | | Composition (%) | |
|---|---|---|---|
| | | This invention | Comparative Products |
| Component | | E | F |
| Oil phase | Vaseline | 18.0 | 18.0 |
| | Liquid paraffin | 14.0 | 14.0 |
| | Bees wax | 4.0 | 4.0 |
| | Liquid lanolin | 8.0 | 8.0 |
| | Cetyl palmitate | 4.0 | 4.0 |
| | Isostearyl phosphate* | 0.5 | — |
| | Sorbitan sesquioleate (HLB 3.7) | 3.5 | 4.2 |
| Aqueous phase | Propylele glycol | 3.0 | 3.0 |
| | Sodium benzoate | 0.5 | 0.5 |
| | L-arginine | 0.20 | 0.2 |
| | Water | balance | balance |
| Perfume | | trace | trace |

*Essentially comprising those having monoester:diester ratio = 80:20 and branched chain configuration in the form of a β-branched alkyl represented by the formula (IV) with k = 6 and l = 8.

Method of preparation:
The oil phase was heated to 70°–80° C. and uniformly melted under agitation. The aqueous phase heated to dissolve at 70°–80° C. under agitation was added to conduct emulsification. After cooled to 50° C., a perfume was added and further cooled to 30°–35° C. while stirring. Thereafter, they were further processed and sufficiently emulsified in a homogenizer to obtain nutritive creams.

Result:

TABLE 23

| | | Emulsified state | Stability for emulsification (after one month leaving) | | |
|---|---|---|---|---|---|
| | | | −5° C. | room temperature | 40° C. |
| This invention | E | good | no change | no change | no change |
| Comparative product | F | good | partially separated | no change | separated |

As can be seen from Table 23, the product according to this invention exhibited better stability for emulsification against temperature change as compared with comparative product.

EXAMPLE 15

Cold cream:
Composition:

| (Oil phase) | |
|---|---|
| Liquid paraffin | 25.0% |
| Vaseline | 18.0 |
| Bees wax | 2.0 |
| Cetanol | 3.0 |
| Isocetyl phosphate (same as the phosphoric acid ester* in Table 20) | 1.0 |
| Sorbitan mono-oleate (HLB 4.3) | 2.0 |
| Butylparaben | 0.1 |
| (Aqueous phase) | |
| Propylene glycol | 4.0 |
| Sodium hydroxide | 0.12 |
| Methylparaben | 0.1 |
| Water | balance |
| (Perfume) | trace |

Method of preparation:
The creams were prepared in the procedures similar to Example 11.

EXAMPLE 16

Foundation Cream:

shown in Table 24. The symbols used in the Table mean "extremely good" by ●, "good" by ○ and "somewhat poor" by Δ.

TABLE 24

| Sodium hydroxide to phosphoric acid ester molar ratio | pH | Emulsified state | Stabilization for emulsification after three months at room temperature | after three months at 40° C. | Viscosity (cPs) after one week at 25° C. | after two months at 25° C. |
|---|---|---|---|---|---|---|
| 0.05 | — | immediately separated | — | — | — | — |
| 0.2 | 5.1 | ○ | ○ | Δ | 52,000 | 39,000 |
| 0.5 | 5.9 | ● | ● | ● | 56,000 | 60,000 |
| 0.8 | 6.3 | ● | ● | ● | 63,000 | 66,000 |
| 1.4 | 7.0 | ○ | ○ | Δ | 44,000 | 32,000 |
| 2.0 | — | immediately separated | — | — | — | — |

Composition:

| (Oil phase) | |
|---|---|
| Squalene | 10.0% |
| Isopropyl palmitate | 3.0 |
| Cetyl palmitate | 3.0 |
| Isostearyl phosphate (same as the phosphoric acid ester* in Table 15) | 1.0 |
| Glycerin mono-stearate (HLB 3.5) | 2.0 |
| Butylparaben | 0.1 |
| (Aqueous phase) | |
| Propylene glycol | 5.0 |
| Potassium hydroxide | 0.13 |
| Montmorillonite | 1.0 |
| Titanium oxide | 7.0 |
| Talc | 5.0 |
| Iron oxide | 3.0 |
| Methylparaben | 0.1 |
| Water | balance |
| (Perfume) | trace |

Method of preparation:

The oil phase was heated to melt at 75°–80° C. and uniformly mixed under agitation. While on the other hand, the aqueous phase was heated to dissolve at 70°–75° C. After uniformly dispersing the powder in a dispersing machine, the oil phase was added and reacted to conduct emulsification. After cooled to 50° C. while stirring, a perfume was added, further cooled to 30°–40° C. and then processed and sufficiently emulsified in a homogenizer to obtain foundation cream.

EXAMPLE 17

For the moisture cream A in Table 15 of Example 11, the emulsified state, the stabilization for emulsification and the changes in physical properties therefor were examined while varying the blending ratio (molar ratio) of the basic substance (sodium hydroxide) to phosphoric acid ester from 0.05 to 2.0. The results are as As can be seen from Table 24, in the case where the sodium hydroxide to phosphoric acid ester molar ratio is within a range of 0.2–1.8, the moisture cream prepared is neutral or weakly acidic nature. Particularly, when the above molar ratio is within a range of 0.4–1.4, the aging changes in the viscosity is low and the stability for emulsification is satisfactory.

EXAMPLE 18

A functional test was conducted by 10 expert panelers for the feelings in actual use of the moisture cream S in Example 11 and the nutritive milky lotion A in Example 13 as the products according to this invention, the moisture creams G, H as comparative products and the nutritive milky lotion I as commercial products shown in Table 25, that, for 5 specimens in total. The results are shown in Table 26.

TABLE 25

| | | Composition (%) | |
|---|---|---|---|
| Component | | This invention G | Comparative product H |
| Oil phase | Vaseline | 6.0 | 6.0 |
| | 2-octyldodecyl myristate | 10.0 | 10.0 |
| | Cetanol | 2.0 | 2.0 |
| | Cetyl palmitate | 6.0 | 6.0 |
| | Stearic acid | 2.0 | — |
| | Glycerin monostearate | 2.0 | 3.0 |
| | Butylparaben | 0.1 | 0.1 |
| Aqueous phase | Glycerin | 5.0 | 5.0 |
| | Sodium cetyl sulfate | — | 0.6 |
| | Triethanolamine | 1.0 | — |
| | Methylparaben | 0.1 | 0.1 |
| | Water | balance | balance |
| Perfume | | trace | trace |

Method of preparation:

The preparation procedures were the same as in Example 11.

TABLE 26

| | Specimen | Appearance | Extendability | Affinity to skin | Stickiness |
|---|---|---|---|---|---|
| This invention | S (Moisture cream) | +1.6 | +1.0 | +1.8 | −1.2 |
| | A (Nutritive milky lotion) | +1.8 | +2.0 | +1.6 | −1.8 |
| Comparative products | G (Moisture cream) | +1.2 | +0.4 | −1.2 | +1.0 |
| | H (Moisture cream) | +0.2 | −1.0 | −1.4 | +1.4 |
| | I | +1.4 | +1.6 | +0.4 | −0.8 |

TABLE 26-continued

|  | (Commercial Nutritive milky lotion) |
| --- | --- |

(The values are averaged values for 10 personels)
(Estimation standard)

| | Appearance, Extendability, Affinity to skin | Stickiness |
| --- | --- | --- |
| +2 | extremely good | extremely strong |
| +1 | good | rather strong |
| 0 | usual | usual |
| −1 | somewhat poor | weak |
| −2 | poor | extremely weak |

As can be seen from Table 26, the specimens S and A as the products according to this invention exhibited good affinity to human skins and less stickiness and gave good results.

What is claimed is:

1. An emulsified cosmetic, consisting essentially of the following components (a) to (d):

(a) 0.1 to 5 wt% of a neutralized product of a phosphoric acid ester which is neutralized with 0.2 to 1.8 times on a molar basis of a basic substance selected from the group consisting of an alkali metal hydroxide, a basic amino acid and an alkanolamine, said phosphoric acid ester containing a phosphoric acid monoester represented by formula (Ia) and a phosphoric acid diester represented by formula (IIa) in a molar ratio ranging from 100:0 to 70:30:

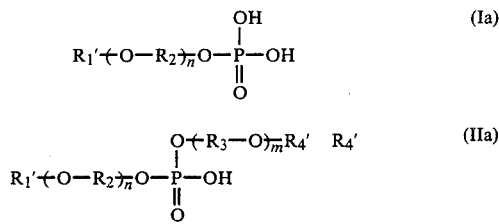

wherein $R_1'$ and $R_4'$ each represent a linear alkyl group or a linear alkenyl group of 10 to 22 carbon atoms, $R_2$ and $R_3$ each represent an ethylene group or a propylene group and m and n are each a number of 0 to 30;

(b) 0.1 to 20 times by weight the amount of component (a) of a nonionic surfactant with an HLB value of up to 6, said nonionic surfactant being selected from the group consisting of polyoxyalkylene alkyl ether, polyoxyalkylene alkenyl ether, polyoxyalkylene alkylphenyl ether, polyoxyalkylene fatty acid ester, polyoxyalkylene glycerin fatty acid ester, polyoxyalkylene sorbitan fatty acid ester, polyoxyalkylene hardened castor oil, polyoxyalkylene alkyl amide, glycerin fatty acid ester, sorbitan fatty acid ester, sucrose fatty acid ester, polyglycerin fatty acid ester, ethylene or propylene glycol fatty acid ester, and fatty acid alkanolamide;

(c) 1 to 60 wt% of an oily substrate selected from the group consisting of hydrocarbons, wax, natural oil and fat of animal and vegetable origin, silicone oil, fatty acid, higher alchol, and ester reaction products of said higher alcohol and said fatty acid; and (d) 25 to 95 wt% of water.

2. The emulsified cosmetic according to claim 1, wherein said basic substance in component (a) is arginine.

3. The emulsified cosmetic of claim 1, wherein the amount of component (a) is 0.3–3% by wt., the amount of component (b) is 0.3–12 time the weight of component (a), the amount of component (c) is 5–35% by weight and the amount of water (d) is 40–90% by weight.

4. The emulsified cosmetic of claim 1, wherein the ratio of phosphoric acid mono ester to phosphoric acid diester in component (a) ranges from 100:0 to 80:20.

5. The emulsified cosmetic of claim 1, wherein said basic amino acid is a member selected from the group consisting of arginine, ornithine, lysine and oxylysine.

6. The emulsified cosmetic of claim 1, wherein said alkanolamine contains two or three carbon atoms.

7. The emulsified cosmetic of claim 1, wherein the amount of said basic substance utilized to neutralize said phosphoric acid ester ranges from 0.4–1.0 mole of basic substance per mole of phosphoric acid ester.

8. The emulsified cosmetic of claim 1, which further comprises at least one other cosmetic material selected from the group consisting of surfactants, viscosity controllers, pharmaceutical agents, corrosion inhibitors, wetting agents, pigments and perfumes.

9. The emulsified cosmetic of claim 1, wherein said cosmetic is a vanishing cream.

10. A vanishing cream, consisting essentially of (a) 0.1 to 5 wt% of a neutralized product of a phosphoric acid ester which is neutralized with 0.2 to 1.8 times on a molar basis of a basic substance selected from the group consisting of an alkali metal hydroxide, a basic amino acid and an alkanolamine, said phosphoric acid ester containing a phosphoric acid monoester represented by formula (Ia) and a phosphoric acid diester represented by formula (IIa) in a molar ratio ranging from 100:0 to 70:30:

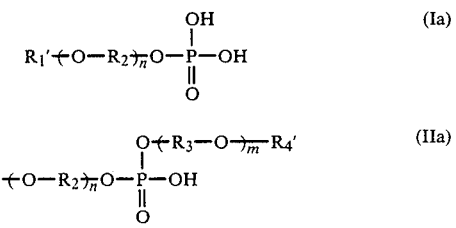

wherein $R_1'$ and $R_4'$ each represent a linear alkyl group or a linear alkenyl group of 10 to 22 carbon atoms, $R_2$ and $R_3$ each represent an ethylene group or a propylene group and m and n are each a number of 0 to 30;

(b) 0.1 to 20 times by weight the amount of component (a) of a nonionic surfactant with an HLB value of up to 6, said nonionic surfactant being selected from the group consisting of polyoxyalkylene alkyl ether, polyoxyalkylene alkenyl ether, polyoxyalkylene alkylphenyl ether, polyoxyalkylene fatty acid ester, polyoxyalkylene glycerin fatty acid ester, polyoxyalkylene sorbitan fatty acid ester, polyoxyalkylene hardened castor oil, polyoxyalkylene alkyl amide, glycerin fatty acid ester, sorbitan fatty acid ester, sucrose fatty acid ester, polyglycerin fatty acid ester, ethylene or propylene glycol fatty acid ester, and fatty acid alkanolamide;

(c) 1 to 60 wt% of an oily substrate selected from the group consisting of hydrocarbons, wax, natural oil and fat of animal and vegetable origin, silicone oil, fatty acid, higher alcohol, and ester reaction products of said higher alcohol and said fatty acid; and (d) 25 to 95 wt% of water.